(12) United States Patent
Yamashita et al.

(10) Patent No.: US 8,987,447 B2
(45) Date of Patent: Mar. 24, 2015

(54) THIENOPYRAZINE COMPOUND AND FIELD EFFECT TRANSISTOR CONTAINING THE SAME

(75) Inventors: Yoshiro Yamashita, Yokohama (JP); Hikaru Nakayama, Yokohama (JP); Takashi Sugioka, Kurashiki (JP)

(73) Assignees: Kuraray Co., Ltd., Kurashiki-shi (JP); Tokyo Institute of Technology, Tokyo (JP)

( * ) Notice: Subject to any disclaimer, the term of this patent is extended or adjusted under 35 U.S.C. 154(b) by 77 days.

(21) Appl. No.: 13/514,371

(22) PCT Filed: Dec. 6, 2010

(86) PCT No.: PCT/JP2010/071829
§ 371 (c)(1),
(2), (4) Date: Jun. 7, 2012

(87) PCT Pub. No.: WO2011/071018
PCT Pub. Date: Jun. 16, 2011

(65) Prior Publication Data
US 2012/0248428 A1   Oct. 4, 2012

(30) Foreign Application Priority Data
Dec. 8, 2009 (JP) .................................. 2009-278734

(51) Int. Cl.
*C07D 495/14* (2006.01)
*C07D 495/04* (2006.01)
*H01L 51/00* (2006.01)
*H01L 51/05* (2006.01)

(52) U.S. Cl.
CPC .......... *C07D 495/04* (2013.01); *H01L 51/0068* (2013.01); *H01L 51/0072* (2013.01); *H01L 51/0558* (2013.01); *H01L 51/0053* (2013.01); *H01L 51/0071* (2013.01)
USPC ....................................................... 544/345

(58) Field of Classification Search
CPC ...................................................... C07D 495/14
USPC ........................................................ 544/345
See application file for complete search history.

(56) References Cited

FOREIGN PATENT DOCUMENTS

| JP | A-11-40356 | 2/1999 |
| JP | A-2007-266411 | 10/2007 |
| WO | WO 2006/113205 A2 | 10/2006 |

OTHER PUBLICATIONS

Jan. 18, 2011 International Search Report issued in International Patent Application No. PCT/JP2010/071829.
Mori et al., "Evaluation and Application of Organic Transistor Material II," *High Technology Information*, 2008, pp. 32-48 and pp. 81-94, CMC Publishing Co., Ltd.
Aqad et al., "Intramolecular Charge-Transfer Interactions-inn-Extended Tetrathiafulvalene Derivatives," *Journal of Organic Chemistry*, 2005, pp. 768-775, vol. 70, No. 3.
Pohmer et al., "Synthesis of Thieno[3,4-b]quinoxaline and Derivatives," *Journal of Organic Chemistry*, 1995, pp. 8283-8288, vol. 60, No. 25, American Chemical Society.
Aqad et al., "Synthesis of Stable Seleno[3,4-b]quinoxaline Derivatives," *Organic Letters*, 2003, pp. 4089-4092, vol. 5, No. 22, American Chemical Society.
Echinger et al., "New Arenemethylenes for the Synthesis of Low Band Gap Polymers," *Synthetic Materials*, 1995, pp. 695 and 696, vol. 69, No. 1-3, Elsevier Science.
Hanack et al., "Investigations on the configuration of new arenemethylenes for the synthesis of low bandgap polymers," *Synthetic Materials*, 1996, pp. 43-47, vol. 79, No. 1, Elsevier Science.
Mar. 18, 2013 Extended European Search Report issued in European Application No. 10835938.1.

*Primary Examiner* — Douglas M Willis
(74) *Attorney, Agent, or Firm* — Oliff PLC

(57) ABSTRACT

A thienopyrazine compound which is useful for an organic semiconductor material. An organic field effect transistor, which includes an organic semiconductor layer that is easily produced from an organic semiconductor material containing the thienopyrazine compound by a coating method or a printing method, and which exhibits high carrier mobility and high on/off current ratio; and an organic field effect transistor which has ambipolar characteristics. The thienopyrazine compound is represented by chemical formula (I):

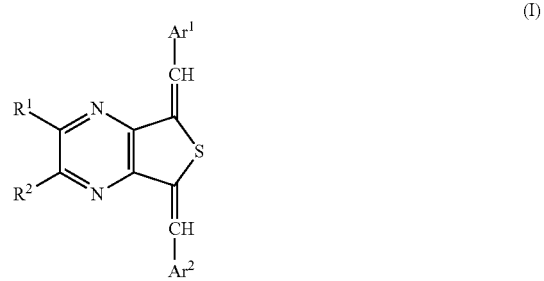

(I)

wherein $Ar^1$ and $Ar^2$ each represents an aryl group, and $R^1$ and $R^2$ each independently represents a hydrogen atom, an alkyl group or an aryl group; or alternatively $R^1$ and $R^2$ represent a group having a ring formed by combining $R^1$ and $R^2$ together.

8 Claims, 2 Drawing Sheets

THIENOPYRAZINE COMPOUND AND FIELD EFFECT TRANSISTOR CONTAINING THE SAME

TECHNICAL FIELD

The present invention relates to a thienopyrazine compound which is useful for an organic semiconductor material and also to an organic field effect transistor containing the compound which works as a carrier mobility layer.

BACKGROUND OF THE INVENTION

Field effect transistors, as well as bipolar transistors, are widely used as important switches or amplifying elements. The transistor comprises: a semiconductor layer which forms a current path between a source electrode and a drain electrode; a gate electrode which controls the flow of the current by applying voltage; and an insulator layer which separates the gate electrode from the semiconductor layer. The characteristics of the field effect transistor are determined by characteristics of a semiconductor to be used. In particular, the carrier mobility and on/off value are important factors.

Inorganic materials such as amorphous silicon, polysilicon, etc. have been widely used as semiconductor materials. Inorganic semiconductor material typically represented by silicon is a single crystal of a single element, has a simple structure and is stable in physical properties. However, such silicon needs high temperature treatments so that it is difficult for a plastic base plate or film to be used as a substrate for field effect transistors. In addition, expensive manufacturing facilities are required because devices are produced under vacuum environment, being expensive.

Recently, instead of the inorganic semiconductors, organic field effect transistors using organic semiconductors are attracting attention, and studies on the organic semiconductors have been recently proceeded with great speed in terms of fundamental optoelectronics. These organic field effect transistors enable the production of light-weight, mechanically-flexible and large-area transistors by using organic semiconductors.

Organic semiconductors are classified into 3 types: a p-type semiconductor in which a positively charged hole has a role of transmitting electrical current; an n-type semiconductor in which a negatively charged free electron has a role of transmitting electrical current; and an ambipolar type semiconductor which has both p-type and n-type roles.

For example, Japanese Patent Publication 2007-266411A discloses a field effect transistor that uses a benzodifuranone-type organic compound as a semiconductor material. This field-effect transistor has n-type, p-type and ambipolar-type electrical characteristics.

A number of organic semiconductors having p-type characteristics are just starting developing in recent years, but the development of the p-type organic transistors is still insufficient. As for the n-type and ambipolor-type organic semiconductors, the number itself of the studies on their materials has been very small so far.

Desired are organic semiconductor materials, regardless of transistor type (n-type, p-type, or ambipolar type), having high carrier mobility and high on/off ratio, and also having excellent processability such that a solution of organic semiconductor material can be, coated or printed using an ink-jet printing technique. In particular, desired are the development of organic semiconductor materials from which a low-power-consumption complementary-type metal-oxide semiconductor (CMOS) circuit can be easily produced, because a transistor made of ambipolar-type organic semiconductor makes the transistor possible to have both p-type and n-type drive. (Evaluation and Application of Organic Transistor Materials II, CMC Publishing Co., LTD, 2008, pp. 81-94)

Organic semiconductor materials at present have little practicability due to its poor solubility, difficulty in synthesis, and insufficient carrier mobility, etc.

SUMMARY OF THE INVENTION

The present invention is made to solve the aforementioned problems. An object of the present invention is; to provide a thienopyrazine compound which is useful for an organic semiconductor material, to provide an organic field effect transistor whose organic semiconductor layer is easily formed through coating or printing technique using the organic semiconductor material containing the thienopyrazine compound, the transistor showing high carrier mobility and on/off current ratio; and further to provide an organic field effect transistor having ambipolar-type characteristics.

A thienopyrazine compound developed to achieve the aforementioned objects of the present invention is represented by the following chemical formula (I)

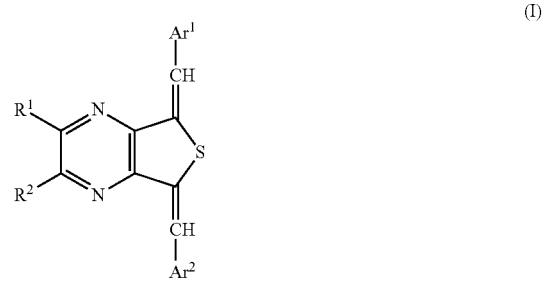

wherein $Ar^1$ and $Ar^2$ each represents an aryl group which may have a substituent; $R^1$ and $R^2$ each independently represents a hydrogen atom, an alkyl group which may have a substituent, or an aryl group which may have a substituent, or alternatively $R^1$ and $R^2$ represent a group having a ring formed by combining $R^1$ and $R^2$ together.

The thienopyrazine compound of the present invention comprises the group having the ring formed by combining $R^1$ and $R^2$ together represented by the following chemical formula

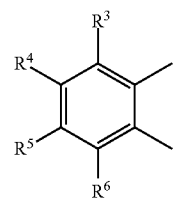

wherein $R^3$ to $R^6$ each independently represents a hydrogen atom, an alkyl group which may have a substituent, or an aryl group which may have a substituent.

The thienopyrazine compound of the present invention comprises the compound represented by the following chemical formula (II)

(II)

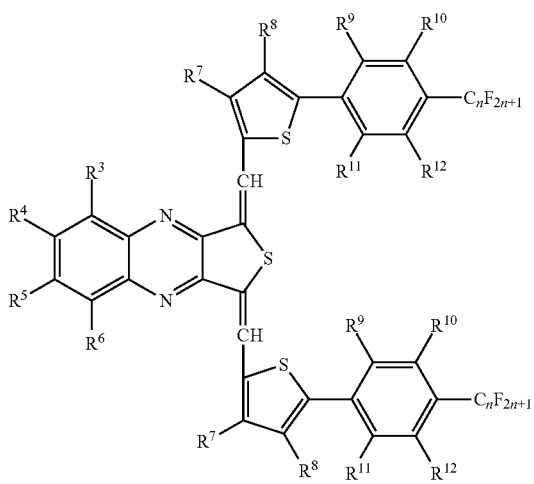

wherein $R^3$ to $R^6$ are the same groups as represented by $R^3$ to $R^6$ of the group having the ring formed by combining $R^1$ and $R^2$ together; $R^7$ to $R^{12}$ each independently represents a hydrogen atom, a hydrocarbon group which has a carbon number of 1-20 and may have a substituent, or an aryl group which may have a substituent; and n is a positive number of 1-20.

An organic semiconductor material of the present invention contains a thienopyrazine compound represented by the following chemical formula (I)

(I)

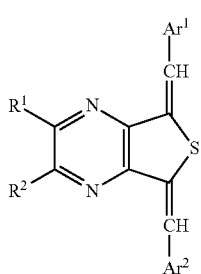

wherein $Ar^1$ and $Ar^2$ each represents an aryl group which may have a substituent; $R^1$ and $R^2$ each independently represents a hydrogen atom, an alkyl group which may have a substituent, or an aryl group which may have a substituent, or alternatively $R^1$ and $R^2$ represent a group having a ring formed by combining $R^1$ and $R^2$ together.

The organic semiconductor material of the present invention contains the thienopyrazine compound, wherein the group having the ring formed by combining $R^1$ and $R^2$ together is represented by the following chemical formula

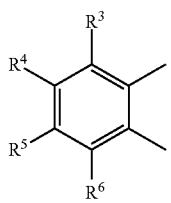

wherein $R^3$ to $R^6$ each independently represents a hydrogen atom, an alkyl group which may have a substituent, or an aryl group which may have a substituent.

The organic semiconductor material of the present invention contains the thienopyrazine compound represented by the following chemical formula (II)

(II)

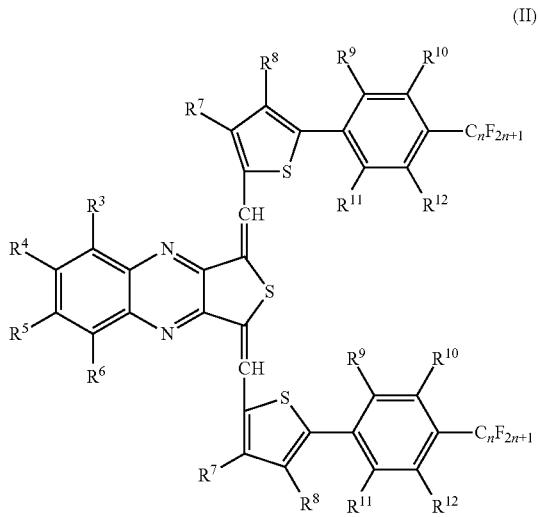

wherein $R^3$ to $R^6$ are the same groups as represented by $R^3$ to $R^6$ of the group having the ring formed by combining $R^1$ and $R^2$ together; $R^7$ to $R^{12}$ each independently represents a hydrogen atom, a hydrocarbon which has a carbon number of 1 to 20 which may have a substituent, or an aryl group which may have a substituent; and n is a positive number of 1 to 20.

An organic field effect transistor of the present invention, in which, on a base plate, an organic semiconductor layer which forms a current path between a source electrode and a drain electrode, is separated, by an insulator layer, from a gate electrode which controls an electric current of the current path; and the organic semiconductor layer contains a thienopyrazine compound represented by the following chemical formula (I)

(I)

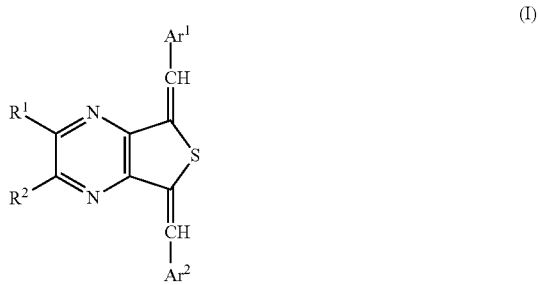

wherein $Ar^1$ and $Ar^2$ each represents an aryl group which may have a substituent; $R^1$ and $R^2$ each independently represents a hydrogen atom, an alkyl group which may have a substituent, or an aryl group which may have a substituent, or alternatively $R^1$ and $R^2$ represent a group having a ring formed by combining $R^1$ and $R^2$ together.

The organic field effect transistor of the present invention comprises the organic semiconductor having ambipolar characteristics.

The thienopyrazine compound of the present invention can be used as an organic semiconductor material that has n-type characteristics or p-type characteristics. In addition, the organic semiconductor material can also be used as a material showing ambipolar characteristics which exhibits both n-type and p-type characteristics by selecting a structure of this thienopyrazine compound.

This organic semiconductor material can be easily formed into a film not only by vapor-deposition processes but also by printing processes such as coating, ink-jetting processes, etc. Accordingly organic field effect transistors can be easily manufactured.

These organic field effect transistors which are made using this organic semiconductor material of the present invention can have high carrier mobility and high on/off current ratio.

The present organic field effect transistors contain in its organic semiconductor layers a thienopyrazine compound so that band gap can be made narrow and ambipolar characteristics can be developed.

DESCRIPTION OF CODES

Figure 1:
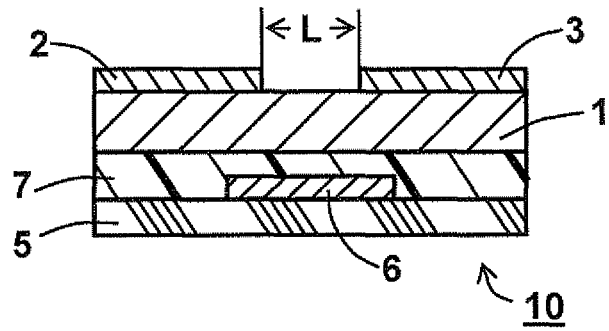
FIG. 1 is a schematic sectional view showing an Example of a top-contact type organic field effect transistor containing the present thienopyrazine compound in an organic semiconductor layer.

1: Organic semiconductor layer
2: Source electrode
3: Drain electrode
5: Insulating supporting substrate
6: Gate electrode
7: Insulating layer
10, 20, 30: Organic field effect transistor
L: Channel length

DETAILED DESCRIPTION OF EMBODIMENTS

A thienopyrazine compound of the present invention is a cis-trans isomer when thiophene unit is made into quinoid form. This isomeric structure can be converted into a cis-cis, cis-trans or trans-trans form when 2 double bonds are arranged into quinoid form. There is no particular limitation on the isomeric structure.

Further, the difference between the Highest Occupied Molecular Orbital (HOMO) and the Lowest Unoccupied Molecular Orbital (LUMO), or the band gap, of the thienopyrazine compound is small. And LUMO level can be regulated by selecting $Ar^1.Ar^2$ and $R^1.R^2$ appropriately in formula (I) shown above.

In formula (I) shown above, the aryl group of $Ar^1$ and $Ar^2$ can be a monocyclic ring or condensed ring and also can be a carbocyclic or heterocyclic compound. As aryl group, for example, thienyl group, furyl group, pyrrolyl group, imidazolyl group, thiazolyl group, phenyl group, naphthyl group, anthryl group, phenanthryl group, fluorenyl group, carbazolyl group, imidazolyl group, pyridyl group, quinolyl group, benzoxazolyl group, benzimidazolyl group, benzothiazolyl group, azepinyl group, etc. can be exemplified. Further a polymer or multimer made from any one of the above mentioned aryl groups or a polymer made from a plurality of different aryl groups mentioned above can also be exemplified. Of them, phenyl group, naphthyl group, thienyl group, and a dimer to eicosamer made of these groups are preferably used.

These aryl groups may have a substituent. As such substituent, for example, an alkyl group such as methyl group, ethyl group, n-propyl group, isopropyl group, n-butyl group, isobutyl group, sec-butyl group, tert-butyl group, n-pentyl group, isopentyl group, neopentyl group, tert-pentyl group, n-hexyl group, isohexyl group, 2-ethylhexyl group, n-heptyl group, n-octyl group, n-nonyl group, n-decyl group, cyclopropyl group, cyclopentyl group, cyclohexyl group, cyclooctyl group, etc.; a perfluoroalkyl group having a carbon number of 1 to 20 made from above-mentioned linear, branched or cyclic alkyl groups (80 to 100% of the hydrogen atoms are substituted by fluorine atoms) such as trifluoromethyl group, pentafluoroethyl group etc.; an aryl group such as phenyl group, naphthyl group, pyridyl group, thienyl group, furyl group, pyrrolyl group, etc.; an alkoxy group such as methoxy group, ethoxy group, n-propyloxy group, isopropyloxy group, n-butoxy group, cyclohexyloxy group, n-octyloxy group, n-decyloxy group, n-dodecyloxy group, etc.; an alkylthio group such as methylthio group, ethylthio group, propylthio group, butylthio group, phenylthio group, naphthylthio group, etc.; a trisubstituted silyloxy group such as tert-butyldimethylsilyloxy group, tert-butyldiphenylsilyloxy group, etc.; an acyloxy group such as acetoxy group, propanoyloxy group, butanoyloxy group, pivaoyloxy group, benzoyloxy group, etc.; an alkoxycarbonyl group such as methoxycarbonyl group, ethoxycarbonyl group, n-butoxycarbonyl group, etc.; a sulfoxide group such as methylsulfoxide group, ethylsulfoxide group, phenylsulfoxide group, etc.; a sulfonic ester group such as methylsulfonyloxy group, ethylsulfonyloxy group, phenylsulfonyloxy group, methoxysulfonyl group, ethoxysulfonyl group, phenyloxysulfonyl group, etc.; a primary or secondary amino group such as dimethylamino group, diphenylamino group, methylphenyl amino group, methylamino group, ethylamino group etc.; an amino group which may be substituted by an alkyl group or aryl group such as methyl group, ethyl group, propyl group, isopropyl group, butyl group, isobutyl group, tert-butyl group, phenyl group, etc.; which are substituted by acetyl group, benzoyl group, benzenesulfonyl group, tert-butoxycarbonyl group, etc.; cyano group; nitro group; a halogen atom such as fluorine atom, chlorine atom, bromine atom, iodine atom, etc. can be exemplified.

Of them, as a preferred example which exhibits ambipolar characteristics, a fluorine atom or a perfluoroalkyl group can be exemplified.

As an alkyl group represented by $R^1$ and $R^2$ in formula (I) shown above, an alkyl group having a carbon number of 1 to 20 such as, for example, a linear or branched alkyl group such as methyl group, ethyl group, propyl group, isopropyl group, butyl group, isobutyl group, sec-butyl group, tert-butyl group, pentyl group, isopentyl group, neopentyl group, tert-pentyl group, hexyl group, iso-hexyl group, 2-ethylhexyl group, heptyl group, octyl group, nonyl group, decyl group, dodecyl group etc.; and a cyclic cycloalkyl group such as cyclopropyl group, cyclobutyl group, cyclopentyl group, cyclohexyl group, cycloheptyl group, cyclooctyl group, cyclononyl group, cyclodecyl group, cycloundecyl group, cyclododecyl group, etc. can be exemplified.

These alkyl groups may have a substituent. As such substituent, for example, an aryl group such as phenyl group, naphthyl group, anthryl group, phenanthryl group, etc.; a heteroaromatic group such as pyridyl group, thienyl group, furyl group, pyrrolyl group, imidazolyl group, pyrazinyl group, oxazolyl group, thiazolyl group, pyrazolyl group, benzothiazolyl group, benzimidozolyl group, etc.; an alkoxy group such as methoxy group, ethoxy group, propoxy group, isopropoxy group, butoxy group, isobutoxy group, sec-butoxy group, tert-butoxy group, pentyloxy group, isopentyloxy group, neopentyloxy group, hexyloxy group, cyclohexyloxy group, heptyloxy group, octyloxy group, nonyloxy group, decyloxy group, dodecyloxy group, etc.; an alkylthio group such as methylthio group, ethylthio group, propylthio group, buthylthio group, etc.; on arylthio group such as phenylthio group, naphthylthio group, etc.; a trisubstituted silyloxy group such as tert-butyldimethylsilyloxy group, tert-butyldiphenylsilyloxy group, etc.; an acyloxy group such as acetoxy group, propanoyloxy group, butanoyloxy group, pivaloyloxy group, benzoyloxy group, etc.; an alkoxycarbonyl group such as methoxycarbonyl group, ethoxycarbonyl group, propoxycarbonyl group, isopropoxycarbonyl group, butoxycarbonyl group, isobutoxycarbonyl group, sec-butoxycarbonyl group, tert-butoxycarbonyl group, pentyloxycarbonyl group, hexyloxycarbonyl group, heptyloxycarbonyl group, octyloxycarbonyl group, etc.; an alkylsulfinyl group such as methylsulfinyl group, ethylsulfinyl group, etc.; an arylsulfinyl group such as phenylsulfinyl group, etc.; a sulphonic acid ester group such as methylsulfonyloxy group, ethylsulfonyloxy group, phenylsulfonyloxy group, methoxysulfonyl group, ethoxysulfonyl group, phenyloxysulfonyl group, etc.; a primary or secondary amino group; cyano group; nitro group; halogen atom such as fluorine atom, chlorine atom, bromine atom, iodine atom, etc.; can be exemplified.

In formula (I) shown above, the aryl group represented by symbols of $R^1$ and $R^2$ can be a monocyclic ring or a condensed ring or can be a carbocyclic or heterocyclic compound. As the aryl group, for example, phenyl group, naphthyl group, anthryl group, phenanthryl group, pyridyl group, thienyl group, furyl group, pyrrolyl group, imidazolyl group, pyrazinyl group, oxazolyl group, thiazolyl group, pyrazolyl group, benzothiazolyl group, benzimidazolyl group, etc. are exemplified. These aryl groups may have a substituent. As such substituent, alkyl groups represented by $R^1$ and $R^2$ can be used.

The alkyl groups and alkoxy groups as exemplified above as the substituents have a carbon number of 1 to 30 and may be linear, branched, or cyclic chain.

$R^1$ and $R^2$ in formula (I), as shown in formula (III) shown below, may be combined together to form a quinoxaline skeleton.

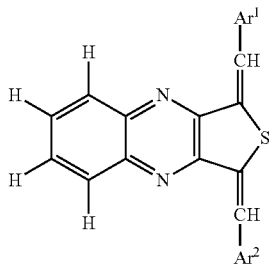

(III)

As shown in the formula (III), the presence of quinoxaline at the acceptor site has a role to control the LUMO level and also to enhance the contribution of quinoid of the quinoid-type thiophene unit that works as a donor site.

In the above-mentioned formula (III), it was shown that $R^3$ to $R^6$ are all hydrogen atoms. However, $R^3$ to $R^6$ each can be an alkyl group having a carbon number of 1 to 20 which may have a substituent, or can be an aryl group which may have a substituent.

Above-mentioned alkyl groups which were exemplified in $R^1$ and $R^2$ can be used for these alkyl groups, and above-mentioned aryl groups which were exemplified in $R^1$ and $R^2$ can also be used for these aryl groups. Such groups may have a substituent. The alkyl groups exemplified in $R^1$ and $R^2$ can be used as such substituent.

As the ring formed by combining $R^1$ and $R^2$ together, as shown in the formula (III), for example, a 6 π electron-based ring such as benzene ring, furan ring, thiophene ring, pyrrole ring, 2H-pyran ring, 4H-thiopyran ring, pyridine ring, oxazole ring, isooxazole ring, thiazole ring, isothiazole ring, furazan ring, imidazole ring, pyrazole ring, pyrazine ring, pyrimidine ring, pyridazine ring, etc.; an 8 π electron-based ring such as pentalene ring, indene ring, indolizine ring 4H-quinolizine ring, etc.; a 10 π electron-based ring such as naphthalene ring, azulene ring, benzofuran ring, isobenzofuran ring, 1-benzothiophene ring, 2-benzothiophene ring, indole ring, isoindole ring, 2H-chromene ring, 1H-2-benzopyran ring, quinoline ring, isoquinoline ring, 1,8-naphthyridine ring, benzimidazole ring, 1H-indazole ring, benzoxazole ring, benzothiazole ring, quinoxaline ring, quinazoline ring, cinnoline ring, pteridine ring, purine ring, phthalazine ring, etc.; a 12 π electron-based ring such as heptalene ring, biphenylene ring, as-indacene ring, s-indacene ring, acenaphthylene ring, fluorene ring, phenalene ring, etc.; a 14 π electron-based ring such as phenanthrene ring, anthracene ring, carbazole ring, xanthene ring, acridine ring, phenanthridine ring, pyrimidine ring, 1,10-phenanthroline ring, phenazine ring, phenarsazine ring, tetrathiafulvalene ring, etc.; a 16 π electron-based ring such as fluoranthene ring, acephenanthrylene ring, aceanthrylene ring, pyrene ring, thianthrene ring, phenoxathiin ring, phenoxazine ring, phenothiazine ring, etc.; an 18 π electron-based ring such as triphenylene ring, chrysene ring, naphthacene ring, pleiadene ring, etc.; a 20 π electron-based ring such as perylene ring, etc.; a 22 π electron-based ring such as picene ring, pentaphene ring, pentacene ring, etc.; a 24 π electron-based ring such as tetraphenylene ring, coronene ring, etc.; a 26 π electron-based ring such as hexaphene ring, hexacene ring, rubicene ring, etc. can be exemplified.

The thienopyrazine compound of the present invention may be the one represented by the above-mentioned formula (II). In the formula (II), as the hydrocarbon groups represented by $R^7$ to $R^{12}$, an alkyl group having a carbon number of 1 to 20, an alkenyl group having a carbon number of 2 to 20 and an alkynyl group having a number of 3 to 20 can be exemplified.

The alkyl group having a carbon number of 1 to 20 can be linear, branched or ring-like one such as, for example, a linear or branched alkyl group such as methyl group, ethyl group, propyl group, isopropyl group, butyl group, isobutyl group, sec-butyl group, tert-butyl group, pentyl group isopentyl group, neopentyl group, tert-pentyl group, hexyl group, isohexyl group, 2-ethylhexyl group, heptyl group, octyl group, nonyl group, decel group, dodecyl group, etc.; and a ring-like cycloalkyl group such as a cyclopropyl group, cyclobutyl group, cyclopentyl group, cyclohexyl group, cycloheptanyl group, cyclooctanyl group, cyclononanyl group, cyclodecanyl group, cycloundecanyl group, cyclododecanyl group, etc. can be exemplified.

As the alkenyl group having a carbon number of 2 to 20, a linear, branched or ring-like group, such as, for example, a vinyl group, allyl group, 1-methylvinyl group, propenyl group, metallyl group, butenyl group, prenyl group, heptenyl group, octenyl group, nonenyl group, dodecenyl group, cyclopentenyl group, cyclohexenyl group, etc. can be exemplified.

As the alkynyl group having a carbon number of 3 to 20, a linear or branched group such as, for example, propynyl group, butynyl group, pentynyl group, hexynyl group, heptynyl group, octynyl group, nonynyl group, dodecynyl group, 1-methyl-2-butynyl group, 1-methyl-3-butynyl group, 2-methyl-3-butynyl group, 3-methyl-1-butynyl group, 3-methyl-2-propynyl group, 2-ethynyl propyl group, etc. can be exemplified. These hydrocarbon groups may have a substituent and above-mentioned substituent exemplified in the alkyl group of $R^1$ and $R^2$ can be used as such substituent.

As the aryl group represented by $R^7$ to $R^{12}$ in formula (II) shown above, the aryl group represented by $R^1$ and $R^2$ can be used. As the substituent, a substituent exemplified at the alkyl group represented by $R^1$ and $R^2$ can be used.

An example of the synthesis of a thienopyrazine compound of the present invention will be described below.

As shown in a chemical equation (A) described below, thienopyrazine compound (1) can be preferably synthesized by reacting dihydro thienopyrazine (2) with aromatic aldehyde compounds (3) and (4) in the presence of a base.

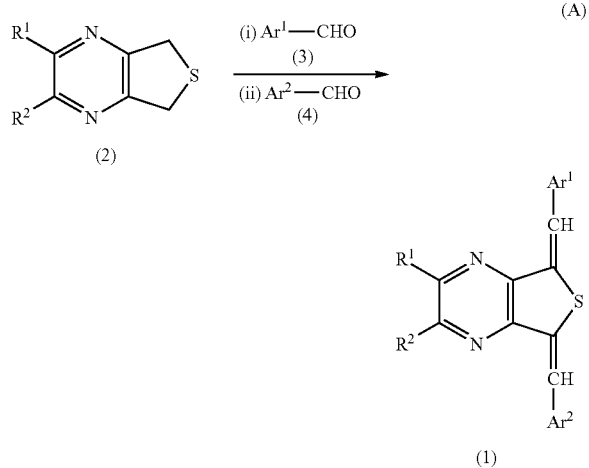

This synthetic reaction is carried out by preferably reacting dihydrothienopyrazine (2) with aromatic aldehyde compound (3) and (4) under an inert gas environment such as argon or nitrogen gas in the presence of solvent.

As a base used in the synthetic reaction, for example, a hydroxide of alkali metal or alkali earth metal such as sodium hydroxide, potassium hydroxide, calcium hydroxide, aluminum hydroxide, etc.; a metal alkoxide such as sodium methoxide, sodium ethoxide, potassium methoxide, lithium methoxide, sodium isopropoxide, sodium tert-buthoxide, potassium tert-buthoxide, magnesium dimethoxide, calcium dimethoxide, etc.; an organic lithium compound such as methyllithium, n-butyllithium, sec-butyllithium, tert-butyllithium, phenyllithium, vinyl lithium, lithium diisopropylamide, lithium bis(trimethylsilyl)amide, etc.; and a tertiary amine such as trimethylamine, triethylamine, tributylamine, trioctylamine, triethanolamine, pyridine, quinoline, etc. can be exemplified.

Of these bases, metal alcoxide or organic lithium compounds can be preferably used. In particular, from the view point of reaction selectivity and availability, potassium tert-butoxide and n-butyllithium are preferable. The amount used is preferably in the range of 0.8 to 5 moles per 1 mole of dihydrothienopyrazine, more preferably 1.0 to 3 moles.

As for the solvent which is used in the synthetic reaction, a solvent can be preferably used as long as dihydrothienopyridine compound (2) and aromatic aldehyde compounds (3) and (4), which are raw materials for the synthesis, are dissolved in the solvent without disrupting the reaction speed and as long as it can be used even in the presence of a base.

As such solvent, an aromatic hydrocarbon such as, for example, benzene, toluene, xylene, ethylbenzene, mesitylene, etc.; an aliphatic hydrocarbon such as pentane, hexane, heptane, octane, nonane, decane, etc.; an alicyclic hydrocarbon such as cyclohexane, cyclooctane, etc.; an ether such as diethyl ether, diisopropyl ether, dibuthyl ether, anisole, tetrahydrofuran, etc. and a mixed solvent thereof, can be exemplified. Of them, an ether represented by tetrahydrofuran is preferably used. The amount of the solvent to be used is preferably 1 to 500 parts by mass per 1 part by mass of dihydrothienopyridine compound (2), and more preferably 3 to 100 parts by mass.

The reaction temperature is preferably in the range of $-80°$ C. to $100°$ C., more preferably in the range of $-20°$ C. to $50°$ C.

As for reaction time, it differs according to the type of dihydrothienopyrazine compound (2), the nature of base and solvent, ratio of amount to be used thereof, and reaction temperature, but is preferably in the range of 0.5 to 30 hours.

The thus obtained thienopyrazine compound (1) is isolated and purified through a conventional method of isolation and purification for organic compounds. For example, reaction mixture is separated into an organic layer and water layer using a separating funnel. Extraction is carried out from the water layer using solvent such as diethylether, ethylacetate, toluene, methylene chloride, 1,2-dichloroethane, etc. The extract is added to the organic layer, then dried under anhydrous sodium sulfate or the like and condensed. Obtained crude product is, if necessary, purified by sublimation, recrystalization, distillation, silica gel column chromatography, etc., obtaining highly-pure thienopyrazine compound (1).

These thienopyrazine compounds have high electron mobility and on/off ratio, and can be used as an organic semiconductor material.

The isomeric structure of the thienopyrazine compound which is used as organic semiconductor material is not particularly limited. Two double bonds in a quinoid type structure have a combination of cis-cis, cis-trans or trans-trans form. One of these structures can be used alone. However, mixture of these structures can also be used. There is almost no energy difference between these isomeric structures as seen from the results of geometry optimization calculation using Gaussian 03.

Organic field effect transistors can be produced by using the organic semiconductor material containing the thienopyrazine compound of the present invention, in preparing an organic semiconductor layer. Further, an organic field effect transistor having ambipolar characteristics can be produced when thienopyrazine compound shown by the above-mentioned formula (II) is used as the organic semiconductor material.

In ambipolar characteristics, the transistor exhibits p-type characteristics when hole is injected and transported as a carrier, and the transistor exhibits n-type characteristics when electron is injected and transported as a carrier.

In an organic field effect transistor, a gate electrode layer to which voltage is applied, an insulator layer, an organic semiconductor layer and a source-drain electrode layer which works as a current path, are laminated on a base plate. Transistor can have various types according to an alignment order of the layers; bottom gate-top contact type, bottom gate-bottom contact type, top gate-bottom contact type and top gate-top contact type.

One of the preferred organic field effect transistors will be explained referring to FIG. 1.

As shown in FIG. 1, in organic field effect transistor 10, gate electrode 6, insulating layer 7, organic semiconductor layer 1 containing thienopyrazine compound, and source-drain electrode layer 2-3 comprising source electrode 2 and drain electrode 3, are laminated sequentially on insulating supporting base plate 5, forming a bottom gate-top contact type transistor. Gate electrode 6 controls the current flow in a current path and is separated from both organic semiconductor 1 and source-drain electrodes 2-3 by insulating layer 7. Source-drain electrode layer 2-3 is deposited on organic semiconductor layer 1 and form a channel region which works as the current path between source electrode 2 and drain electrode 3.

In organic field effect transistor 10, when voltage is applied on gate electrode 6, electric field is generated, and at source-drain electrode layer 2-3, a channel region, which works as a current path between source electrode 2 and drain electrode 3, is formed. At source-drain electrode layer 2-3 and organic semiconductor layer 1, electric current flows when carrier (hole or electron) is moved. Transistor function is operated when carrier density in organic semiconductor layer 1 and insulating layer 7 is changed and the amount of the current flowing between source electrode 2 and drain electrode 3 is changed.

Organic semiconductor layer 1 is formed using the present thienopyrazine compound or the organic semiconductor material containing this compound. Organic semiconductor layer 1 is a carrier-moving layer to move hole or electron, which is a carrier, from one electrode to the other electrode.

Organic semiconductor layer 1 has a film thickness preferably in the range of about 1 nm to 10 μm, more preferably about 10 to 500 nm.

As a row material for insulating supporting base plate 5, polyethylene terephthalate (PET), glass, quartz, silicon, ceramics, plastics, etc. can be exemplified.

The thickness of insulating supporting base plate 5 is preferably in the range of about 0.05 to 2 mm, more preferably about 0.1 to 1 mm.

Leakage current of insulating layer 7 is preferably not more than $10^{-2}$ A/cm$^2$ under electric field intensity of 1.0 MV/cm at room temperature. Relative dielectric constant thereof is normally at around 4.0, a higher value is preferred.

As row materials of insulating layer 7, specifically silicon oxide, silicon nitride, amorphous silicon, aluminum oxide, tantalum oxide, etc. can be exemplified. In addition, insulating layer 7 can be formed from one kind or more than 2 kinds of resin as a main ingredient selected from the group consisting of polystyrene, polyvinylphenol, polycarbonate, polyester, polyvinyl acetate, polyurethane, polysulphone, (meth) acrylic resin, epoxy resin, hydrocarbon resin and phenol resin having cyano group, polyimide resin and polyparaxylene resin.

The film thickness of insulating layer 7 is in the range of about 50 nm to 2 μm, more preferably from about 100 nm to 1 μm.

The raw material for gate electrode 6, source electrode 2, and drain electrode 3 is not particularly limited as long as it has a conductive property. Specifically, platinum, gold, silver, nickel, chrome, copper, iron, tin, antimony lead alloy, tantalum, indium, palladium, tellurium, rhenium, iridium, aluminum, ruthenium, germanium, molybdenum, tungsten, antimony tin oxide, indium tin oxide (ITO), fluorine-doped zinc oxide, zinc, silicone, carbon, graphite, glassy carbon, silver paste, carbon paste, lithium, beryllium, sodium, magnesium, potassium, calcium, scandium, titanium, manganese, zirconium, gallium, niobium, sodium-potassium alloy, magnesium/silver mixture, magnesium/silver mixture, magnesium/aluminum mixture, magnesium/indium mixture, aluminum/aluminum oxide mixture, lithium/aluminum mixture, amorphous silicon, etc. can be exemplified. In addition, publicly well-known conductive polymer such as conductive polyaniline, conductive polypyrrole, conductive polythiophene, complex of polyethylene dioxythiophene and polystyrene sulfonate, etc. can be preferably used.

The film thickness of gate electrode 6, source electrode 2, drain electrode 3 is preferably in the range of 0.01 to 2 μm, more preferably from 0.2 to 1 μm.

Channel length L, the length between source electrode 2 and drain electrode 3, is normally not more than 100 μm, more preferably not more than 50 μm. On the other hand, channel width is normally not more than 2,000 μm, more preferably not more than 500 μm. L/W is normally not more than 0.1, more preferably not more than 0.05.

A method of producing organic field effect transistor 10 is not particularly limited, but conventional methods can be used.

Organic semiconductor layer 1 is made into film by at first dissolving the thienopyrazine compound in a solvent to prepare a solution and then applying the solution using such as casting method, dipping method, spincoating method, etc. or using vacuum deposition method, etc.

Insulator layer 7 can be prepared, for example, using coating method such as spin coating, blade coating, etc., vapor-depositing method, sputtering method, printing method such as screen printing method, ink-jetting method, electrostatic charge image developing method, etc. On the other hand, a monomer, which is a precursor of an insulator, may be applied at first and then the coated monomer is irradiated with light to get a light-cured resin or insulator.

Gate electrode 6, source electrode 2 and drain electrode 3 can be formed by, for example, vacuum deposition method, sputtering method, coating method, printing method, sol-gel method, etc. Further, as their patterning method, printing method such as photolithography method, ink-jet printing method, screen printing method, offset printing method, relief printing method, etc.; a soft lithography technique such as micro contact printing method; and techniques which combine a plurality of these techniques, can be exemplified. On the other hand, patterning can be performed by eliminating material by irradiating the material with energy ray such as LASER, electron ray, etc.

Figure 2:
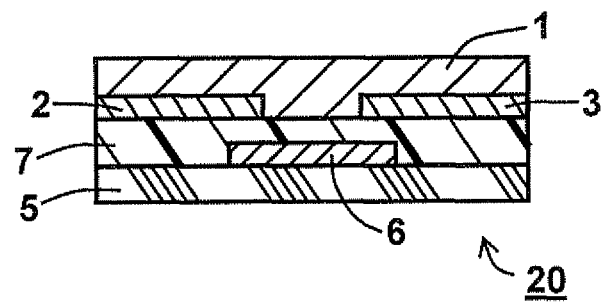
FIG. 2 is a schematic sectional view showing another Example of a bottom-contact type organic field effect transistor containing the present thienopyrazine compound in an organic semiconductor layer.

Next, another example of organic field effect transistor 20 is shown in FIG. 2.

In organic field effect transistor 20 which is a bottom gate-bottom contact type one, gate electrode 6, insulating layer 7, source-drain electrode layer 2-3 having source electrode 2 and drain electrode 3, and organic semiconductor 1 are laminated together in series on insulating base plate 5. This transistor is the same one as shown in FIG. 1 except that the locations of source-drain electrodes 2-3 and organic semiconductor layer 1.

Figure 3:
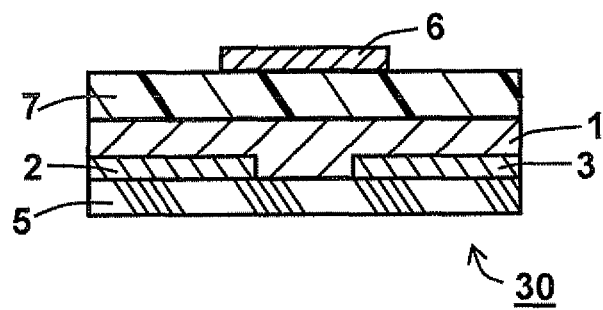
FIG. 3 is a schematic sectional view showing still another Example of an organic field effect transistor containing the present thienopyrazine compound in an organic semiconductor layer.

Still another example of organic field effect transistor 30 is shown in FIG. 3.

In organic field effect transistor 30 is a top gate-bottom contact type, source-drain electrode layer 2-3, organic semiconductor layer 1, insulator layer 7 and gate electrode 6 are laminated together in series on insulator base plate 5.

The structure of the organic field effect transistor is not particularly limited. As shown in FIGS. 1 and 2, in the case where organic semiconductor layer 1 is exposed to the air, a protective film may be formed on organic semiconductor 1. This protective film can minimize the influence from the ambient atmosphere. As the ingredient of the protective film, for example, a polymer such as an epoxy resin, acrylic resin, polyurethane, polyamide, polyvinyl alcohol, etc. an inorganic oxide such as silicon oxide, silicon nitride, aluminum oxide, etc. and nitrides can be exemplified. This protective film can be formed using coating method, vacuum deposition method, etc.

Examples of the present invention will be precisely described below. The scope of the present invention should not be limited by these Examples.

Synthetic Example 1

Synthetic reaction formula (1) of 2,3-bis(bromomethyl) quinoxaline is shown below.

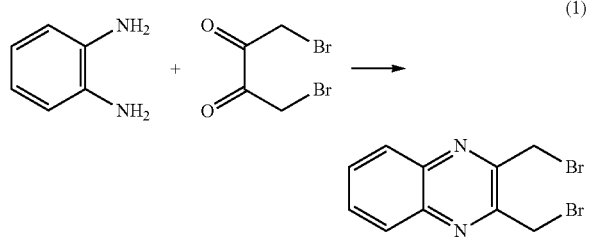

(1)

6.52 g (27 mmol) of 1,4-dibromo-2,3-butanedione and 300 ml of ethanol were placed in a 1,000 ml three-necked flask. To the mixed liquid, a solution which was made by dissolving 2.94 g (27 mmol) of o-phenylenediamine in 150 ml of ethanol, then stirring was continued for 30 minutes at room temperature. White solid was deposited. Into this reaction solution, 200 ml of water was added, and the white solid is suction-filtrated, and then dried under a reduced pressure, obtaining 6.74 g (yield: 81%) of white solid which was the objective substance.

The result of $^1$H magnetic resonance ($^1$H-NMR) analysis of the obtained compound is shown below.

$^1$H-NMR (CDCl$_3$): δ 4.93 (s, 4H), 7.81 (q, 2H), 8.08 (q, 2H)

Synthetic Example 2

Synthetic reaction formula (2) of 1,3-dihydrothieno[3,4-b] quinoxaline is shown below.

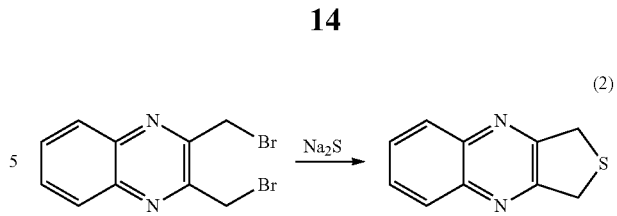

(2)

In a 200 ml three-necked flask, 2.88 g (12 mmol) of sodium sulfide nonahydrate, 70 ml of ethanol and 20 ml of water were transferred at room temperature, then 3.41 g (10.9 mmol) of 2,3-bis(bromomethyl) quinoxaline obtained in Synthetic Example 1 was added and stirring was continued at room temperature for 1 hour. Then 100 ml of toluene was added and organic layer was separated using a separating funnel and the organic layer was washed with a saturated saline water, dried using Na$_2$SO$_4$ and then filtered. Solvent was removed under a reduced pressure environment. The concentrate was recrystallized in hexane, obtaining 1.35 g (yield: 66%) of orange-colored solid object.

The result of $^1$H-NMR analysis of the obtained compound is shown below.

$^1$H-NMR (CDCl$_3$): δ 4.39 (s, 4H), 7.75 (q, 2H), 8.04 (q, 2H)

Synthetic Example 3

Synthetic reaction formula (3) of 5'-hexyl-2,2'-bithiophene-5-carbaldehyde is shown below.

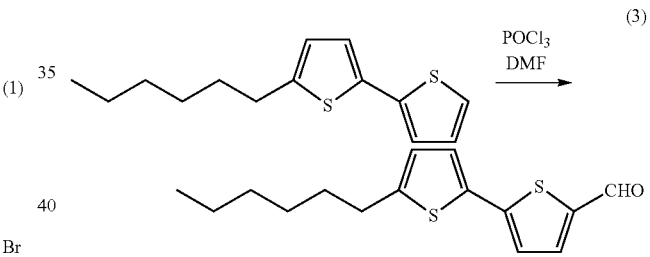

(3)

Into a 50 ml three-necked flask with a dropping funnel, 2.4 g (33 mmol) of N,N-dimethylformamide (DMF) was transferred, and the air was displaced with argon gas, and then 2.2 g (14 mmol) of phosphorous oxychloride (POCl$_3$) was added dropwise at the internal temperature of 10° C., then stirring was continued for 15 minutes. Then 2.50 g (14 mmol) of 2-hexyl-2,2'-bithiophene was added dropwise, stirring was continued at 100° C. for 2 hours. After cooling down to room temperature, stirring was continued overnight. 30 ml of water was added to the reacted solution, and then 30 ml of diethylether was added and the solution was stirred, then an organic layer was separated using a separating funnel. The organic layer was washed with saturated saline water and then dried under anhydrous sodium sulfate and then filtered. Solvent was removed under reduced pressure, obtaining yellow oily substance. The substance was purified using silicagel column chromatography (developing solvent: hexane/ethylacetate=5/1). 0.168 g (yield: 66%) of light-yellowed oily substance was obtained.

The result of $^1$H-NMR analysis of the obtained compound is shown below. $^1$H-NMR (CDCl$_3$): δ 0.87 (t, 3H), 1.25-1.39 (m, 6H), 1.62-1.71 (m, 2H), 2.80 (t, 2H), 6.72 (d, 1H), 7.14 (d, 1H), 7.17 (d, 1H), 7.63 (d, 1H), 9.81 (s, 1H).

Synthetic Example 4

Synthetic reaction formula (4) of 2-(4-trifluoromethylphenyl)thiophene is shown below.

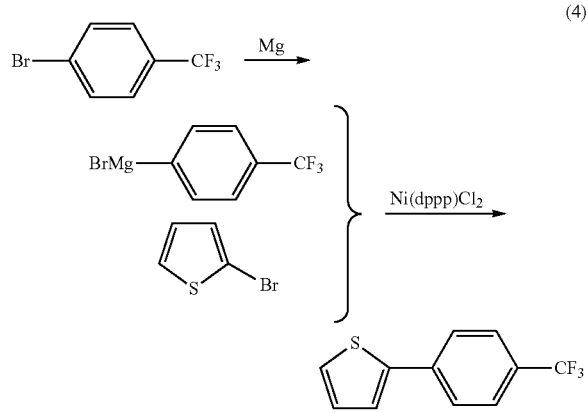

50 ml of tetrahydrofuran and 1.62 g (67 mmol) of magnesium were placed in a 100 ml three-necked flask with a dropping funnel, and the air was displaced with argon gas, 15.0 g (67 mmol) of 4-trifluoromethyl bromobenzene was slowly added dropwise and stirring was carried out for 1 hour to prepare Grignard reagent.

In a 300 ml three-necked flask with a dropping funnel, 50 ml of tetrahydrofuran, 9.8 g (67 mmol) of 2-bromothiophene and 730 mg of Ni (dppp) Cl$_2$ were placed. After the air was displaced with argon gas, the temperature was cooled down to 0° C. To this mixed liquid, previously prepared Grignard reagent was added dropwise with keeping the internal temperature at not higher than 5° C. After the end of dropping, stirring and heating was continued for 12 hours under reflux conditions of tetra hydrofuran. Reaction solution was cooled down to a room temperature, and then 50 ml of saturated ammonium chloride aqueous solution was added. Then 50 ml of diethylether is added and then the organic layer was separated using a separating funnel. This organic layer was washed with saturated saline water, dried under anhydrous magnesium sulfate and then filtrated. Solvent was removed under reduced pressure. This concentrate was purified using silicagel column chlomatography (developing solvent: dichloromethane), obtaining 7.00 g (yield: 51%) of the white solid, the objective substance.

The result of $^1$H-NMR analysis of the obtained compound is shown below.

$^1$H-NMR (CDCl$_3$): δ 7.12 (dd, 1H), 7.36 (dd, 1H), 7.40 (dd, 1H), 7.63 (d, 2H), 7.71 (d, 2H)

Synthetic Example 5

Synthetic reaction formula (5) of 5-(4-trifluoromethylphenyl)thiophene-2-carbaldehyde is shown below.

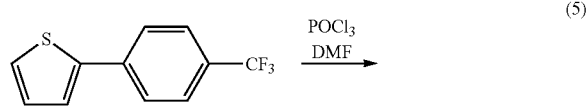

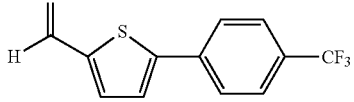

In a 300 ml three-necked flask with a dropping funnel, 40 ml of tetrahydrofuran and 2.0 g (8.76 mmol) of 2-(4-trifluoromethylphenyl)thiophene obtained in Synthetic Example 4 were mixed. After the air was displaced with argon gas, the mixture was cooled down to −78° C. To this mixture, 5.31 ml of hexane solution containing 1.65M n-butyl lithium (8.76 mmol) was added dropwise, with keeping the internal temperature at not higher than −70° C. Stirring was continued for 1 hour after the end of the dropping. Next, 0.64 g (8.76 mmol) of N,N-dimethylformamide was added dropwise with keeping the internal temperature at not higher than −70° C. Stirring was continued for 2 hours after the internal temperature was put back to a room temperature. 50 ml of saturated ammonium chloride aqueous solution was added then 50 ml of diethylether was added, then organic layer was separated using a separating funnel. This organic layer was washed with saturated saline water, dried under anhydrous magnesium sulfate and filtered, then the solvent was removed under reduced pressure. The obtained concentrate was purified using silicagel chromatography (developing solvent: dichloromethane), obtaining 1.68 g (yield: 75%) of white solid, the objective substance.

The result of $^1$H-NMR analysis of the obtained compound is shown below.

$^1$H-NMR (CDCl$_3$): δ 7.48 (d, 2H), 7.69 (d, 2H), 7.79 (d, 2H), 9.91 (s, 1H)

Example 1

Synthetic reaction formula (6) of 1,3-bis(2-thienylmethylen)-1,3-dihydrothieno[3,4-b]quinoxaline is shown below.

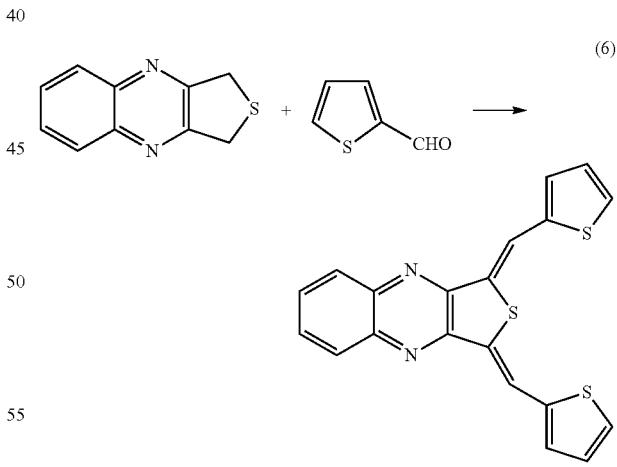

In a 50 ml three-necked flask with a dropping funnel, 1.30 g (11.6 mmol) potassium tert-buthoxide, 1.081 g (6.0 mmol) of 1,3-dihydrothieno[3,4-b]quinoxaline obtained in Synthetic Example 2 and 20 ml of diethylether were placed, and the inside of the system was displaced with argon gas. After stirring was continued for 30 minutes, 6.62 g (59 mmol) of thiophene-2-carbaldehyde was added using a dropping funnel, reaction was carried out for 12 hours at room temperature. Next, the reacted liquid was neutralized with 1N hydrochloride and organic layer was separated using separating funnel. This organic layer was washed with saturated saline water and then dried under magnesium sulfate. Diethylether was eliminated under reduced pressure. 0.232 g (yield: 10.3%) of an amaranth purple-colored solid was obtained by purifying the products using silicagel column chromatography (developing solvent: dichloromethane) and a sublimation process.

The result of $^1$H-NMR analysis of the obtained compound is shown below.

$^1$H-NMR (CDCl$_3$): δ 7.21 (dd, 2H), 7.48 (d, 2H), 7.56 (d, 2H), 7.75 (m, 2H), 8.10 (m, 2H), 8.32 (s, 2H)

Example 2

Synthetic reaction formula (7) of 1,3-bis(phenylmethylene)-1,3-dihydrothieno[3,4-b]quinoxaline is shown below.

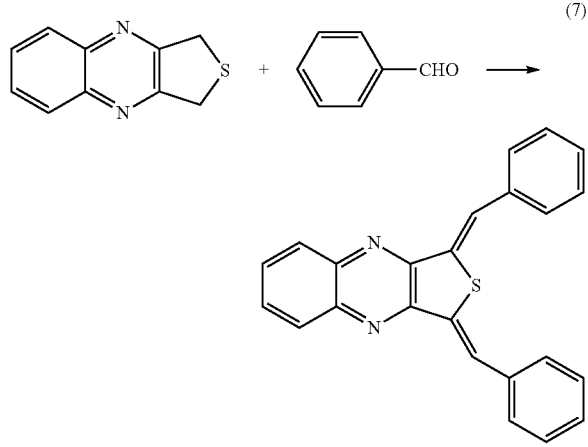

(7)

The same synthetic procedure as described in Example 1 was carried out except that 6.26 g (59 mmol) of benzaldehyde was used instead of 6.62 g (59 mmol) of thiophene-2-carbaldehyde. 0.328 g (yield: 15%) of amaranth purple-colored solid, the objective substance, was obtained.

The result of $^1$H-NMR analysis of the obtained compound is shown below.

$^1$H-NMR (CDCl$_3$): δ 7.37 (s, 2H), 7.53 (t, 4H), 7.79 (m, 4H), 7.80 (m, 2H), 8.15 (q, 2H), 8.16 (s, 2H)

Example 3

Synthetic reaction formula (8) of 1,3-bis(4-trifluoromethylphenylmethylene)-1,3-dihydrothieno[3,4-b]quinoxaline is shown below.

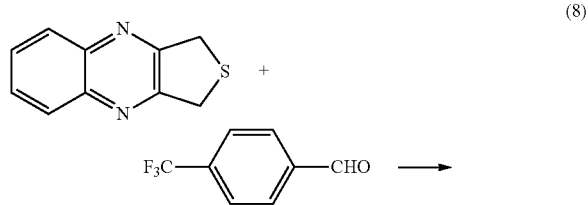

(8)

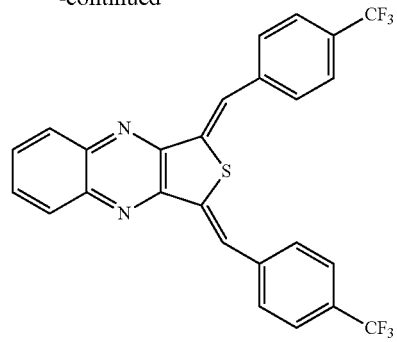

The same synthetic procedure as described in Example 1 was carried out except that 10.27 g (59 mmol) of 4-trifluromethyl benzaldehyde was used instead of 6.62 g (59 mmol) of thiophene-2-carbaldehyde. 0.360 g (yield: 12%) of ocherous-colored solid, the objective substance, was obtained.

The result of $^1$H-NMR analysis of the obtained compound is shown below.

$^1$H-NMR (CDCl$_3$): δ 7.74 (d, 4H), 7.81 (d, 4H), 7.84 (q, 2H), 8.13 (s, 2H), 8.17 (q, 2H)

Example 4

Synthetic reaction formula (9) of 1,3-bis(5-hexyl-2-thienylmethylene)-1,3-dihydrothieno[3,4-b]quinoxaline is shown below.

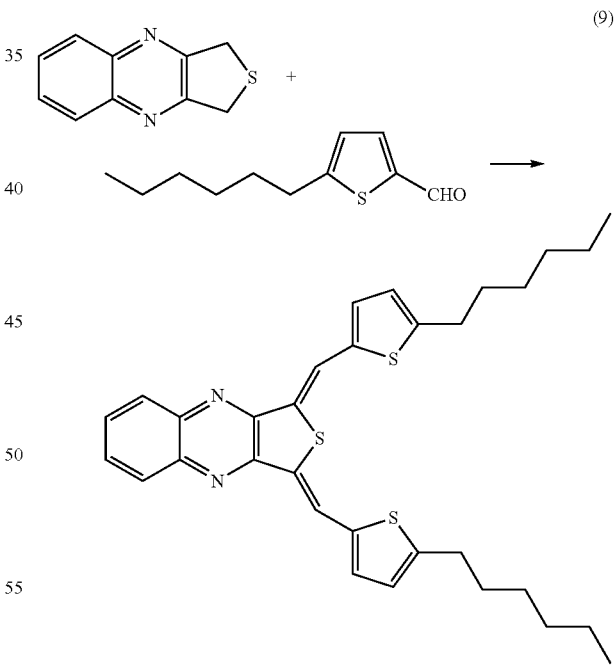

(9)

The same synthetic procedure as described in Example 1 was carried out except that 11.58 g (59 mmol) of 5-hexylthiophene-2-carbaldehyde was used instead of 6.62 g (59 mmol) of thiophene-2-carbaldehyde. 0.523 g (yield: 16%) of amaranth purple-colored solid, the objective substance, was obtained.

The result of $^1$H-NMR analysis of the obtained compound is shown below.

¹H-NMR (CDCl₃): δ 0.90 (s, 6H), 1.25-1.93 (m, 16H), 2.92 (t, 4H), 6.92 (d, 2H), 7.32 (d, 2H), 7.73 (m, 4H), 8.08 (m, 4H), 8.28 (m, 2H)

Example 5

Synthetic reaction formula (10) of 1,3-bis(2,2'-bithienyl-5-yl-methylene)-1,3-dihydrothieno[3,4-b]quinoxaline is shown below.

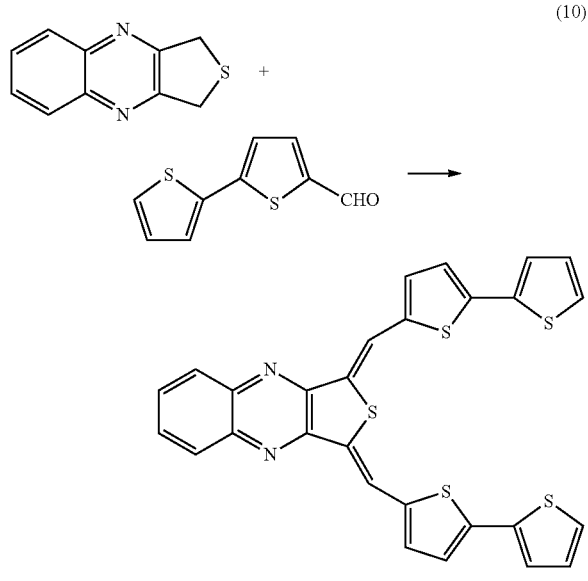

(10)

The same synthetic procedure as described in Example 1 was carried out except that 11.46 g (59 mmol) of 2,2'-bithiophene-5-carbaldehyde was used instead of 6.62 g (59 mmol) of thiophene-2-carbaldehyde. 1.23 g (yield: 38%) of a dark purple-colored solid, the objective substance, was obtained.

The result of ¹H-NMR analysis of the obtained compound is shown below.

¹H-NMR (CDCl₃): δ 7.01 (d, 2H), 7.10 (d, 2H), 7.20 (d, 2H), 7.36 (m, 4H), 7.75 (q, 2H), 8.10 (q, 2H), 8.25 (s, 2H)

Example 6

Synthetic reaction formula (11) of 1,3-bis(biphenyl-4-yl-methylene)-1,3-dihydrothieno[3,4-b]quinoxaline is shown below.

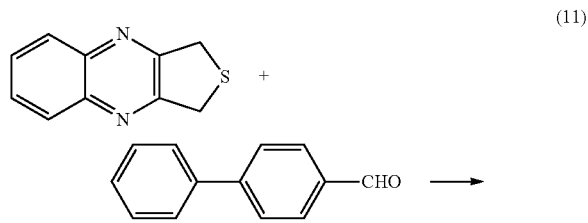

(11)

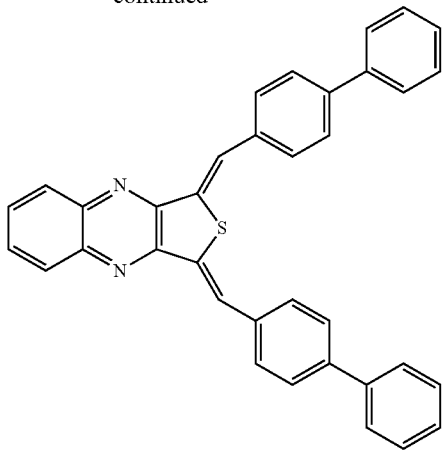

The same synthetic procedure as described in Example 1 was carried out except that 10.75 g (59 mmol) of 4-phenylbenzaldehyde was used instead of 6.62 g (59 mmol) of thiophene-2-carbaldehyde. 0.93 g (yield: 30%) of a red-colored solid, the objective substance, was obtained.

The result of ¹H-NMR analysis of the obtained compound is shown below.

¹H-NMR (CDCl₃): δ 7.40 (d, 2H), 7.49 (d, 4H), 7.67 (d, 4H), 7.81 (d, 4H), 7.82 (m, 2H), 8.17 (q, 2H), 8.20 (s, 2H)

Example 7

Synthetic reaction formula (12) of 1,3-bis(2-naphtylmethylene)-1,3-dihydrothieno[3,4-b]quinoxaline is shown below.

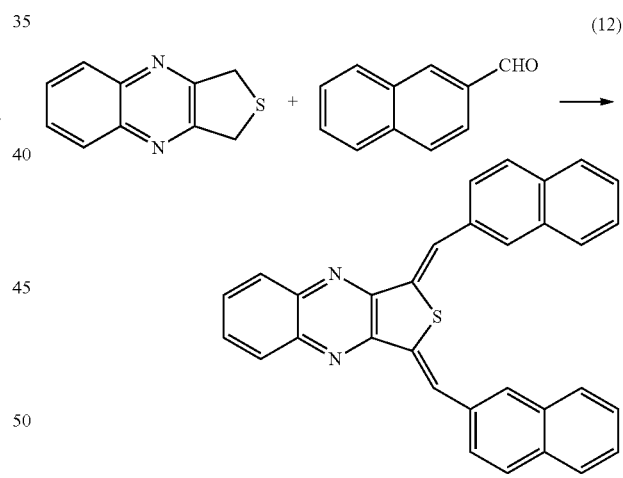

(12)

The same synthetic procedure as described in Example 1 was carried out except that 9.21 g (59 mmol) of 2-naphthaldehyde was used instead of 6.62 g (59 mmol) of thiophene-2-carbaldehyde. 1.20 g (yield: 43%) of red-colored solid, the objective substance, was obtained.

The result of ¹H-NMR analysis of the obtained compound is shown below.

¹H-NMR (CDCl₃): δ 7.55 (m, 8H), 7.82 (q, 2H), 7.93 (m, 3H), 8.20 (q, 2H), 8.33 (s, 2H)

Example 8

Synthetic reaction formula (13) of 1,3-bis(5'-hexyl-2,2'-bithienyl-5-yl-methylene)-1,3-dihydrothieno[3,4-b]quinoxaline is shown below.

(13)

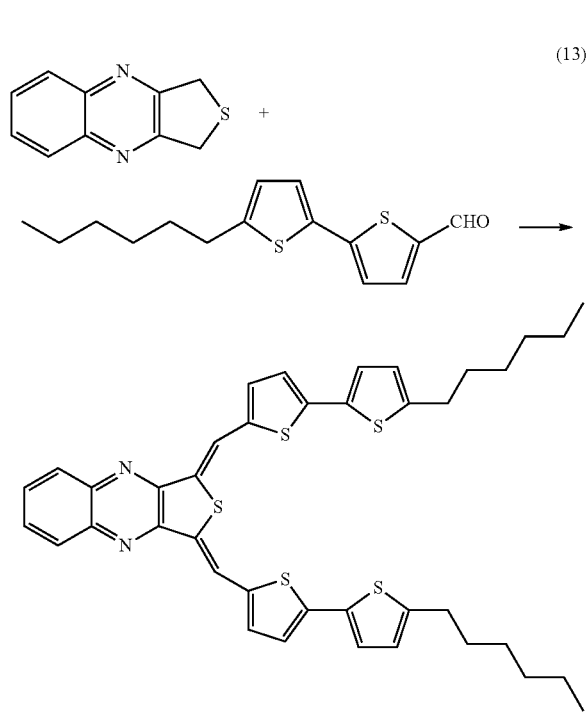

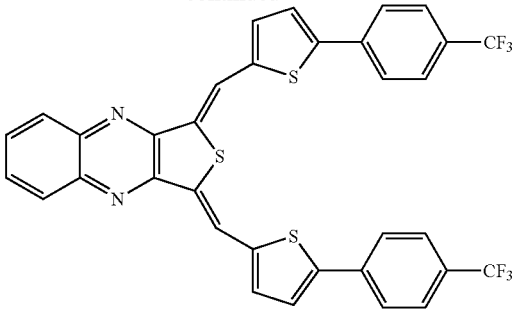

The same synthetic procedure as described in Example 1 was carried out except that 16.42 g (59 mmol) of 5'-hexyl-2,2'-bithiophene-5-carbaldehyde obtained in Synthesis Example 3 was used instead of 6.62 g (59 mmol) thiophene-2-carbaldehyde, and purifying procedure was carried out only by using silicagel column chromatography. 1.19 g (yield: 28%) of purple-colored solid, the objective substance, was obtained.

The result of $^1$H-NMR analysis of the obtained compound is shown below.

$^1$H-NMR (CDCl$_3$): δ 0.94 (m, 6H), 1.24-1.83 (m, 16H), 2.88 (m, 4H), 6.81 (d, 2H), 7.05 (d, 2H), 7.22 (d, 2H), 7.35 (d, 2H), 7.71 (q, 2H), 8.08 (q, 2H), 8.27 (s, 2H)

Example 9

Synthetic reaction formula (14) of 1,3-bis[5-(4-trifluoromethyl)-2-thienylmethylene]-1,3-dihydrothieno[3,4-b]quinoxaline is shown below.

(14)

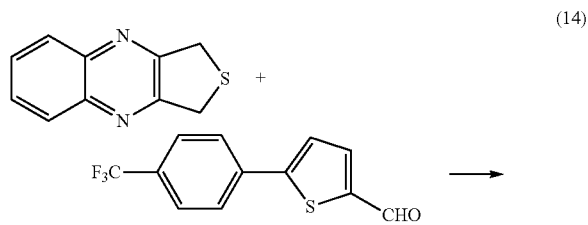

The same synthetic procedure as described in Example 1 was carried out except that 15.12 g (59 mmol) of 5-(4-trifluoromethylphenyl)thiophen-2-carbaldehyde obtained in Synthetic Example 5 was used instead of 6.62 g (59 mmol) of thiophen-2-carbaldehyde. 0.52 g (yield: 13%) of a brown-colored solid, the objective substance, was obtained.

The result of $^1$H-NMR analysis of the obtained compound is shown below.

$^1$H-NMR (CDCl$_3$): δ 7.12 (dd, 2H), 7.38 (dd, 2H), 7.62 (d, 2H), 7.71 (d, 2H), 7.82 (m, 2H), 8.14 (q, 2H), 8.33 (s, 2H)

Example 10

Top Contact-type Organic Field Effect Transistor 3.5×2.5 cm silicon wafer to be used for an insulating-supporting base plate was cut out from the wafer having the thickness of 500 μm. This base plate was subjected to ozone treatment, or to hexamethyldisilazane (HMDS) or octyltrichlorosilane (OTS) treatment after the ozone treatment. On the thus treated supporting base plate, an n-type silicone wafer was formed as a gate electrode. On the gate electrode, a silicon oxide (SiO$_2$) insulating layer having a thickness of 200 nm was formed using a thermal oxidation method.

Next, on the SiO$_2$ layer, 30 nm-thick vacuum-deposited organic semiconductor layer made from compounds obtained in Examples 1, 5, 6, 7, 8 and 9 was formed respectively using vacuum deposition method. Further on the organic semiconductor layers, a 50 nm-thick gold layer was vacuum-deposited, obtaining top contact type organic field effect transistors as shown in FIG. 1. Vapor deposition was carried out so as to obtain the transistors with a channel length of 50, 75 and 100 μm respectively and channel width (W) of 1,000 μm.

The obtained organic field effect transistors were tested to evaluate their transistor characteristics by obtaining current-voltage curve at 25° C. using an electrometer under the conditions that voltages of 10 to 60V was applied between the source and the drain electrodes, and gate voltage was shifted between −20 to 100 V.

A carrier mobility (μ) was calculated using the following formula (A) which expresses a drain current $$I_d = (W/2L) \cdot \mu \cdot Ci \cdot (V_g - V_t)^2 \tag{A}$$

In the formula (A), L is a gate length, W is a gate width. Also Ci is a capacitance per unit area of the insulating layer, $V_g$ is a gate voltage and $V_t$ is a threshold voltage.

An on/off ratio was calculated from the maximum and minimum drain current value ($I_d$).

These obtained transistor characteristics are shown in Table 1.

TABLE 1

| Compound | Transistor characteristics | Forming method of organic semiconductor layer | Carrier mobility (cm²/V·s) | On/Off ratio | Threshold voltage (V) |
|---|---|---|---|---|---|
| Ex. 1 | P type | Vacuum Deposition | $9.4 \times 10^{-5}$ | $1.3 \times 10^{4}$ | 33 |
| Ex. 5 | P type | Vacuum Deposition | $1.5 \times 10^{-4}$ | $2.3 \times 10^{4}$ | 21 |
| Ex. 6 | P type | Coating | $1.0 \times 10^{-4}$ | $2.9 \times 10^{4}$ | 42 |
| Ex. 7 | P type | Vacuum Deposition | $6.1 \times 10^{-4}$ | $1.7 \times 10^{3}$ | 38 |
| Ex. 8 | P type | Coating | $3.1 \times 10^{-5}$ | $1.1 \times 10^{4}$ | 45 |
| Ex. 9 | P type | Vacuum Deposition | $2.8 \times 10^{-6}$ | $1.0 \times 10^{3}$ | 70 |
|  | N type |  | $1.0 \times 10^{-5}$ | $4.8 \times 10^{3}$ | 54 |

Figure 4:
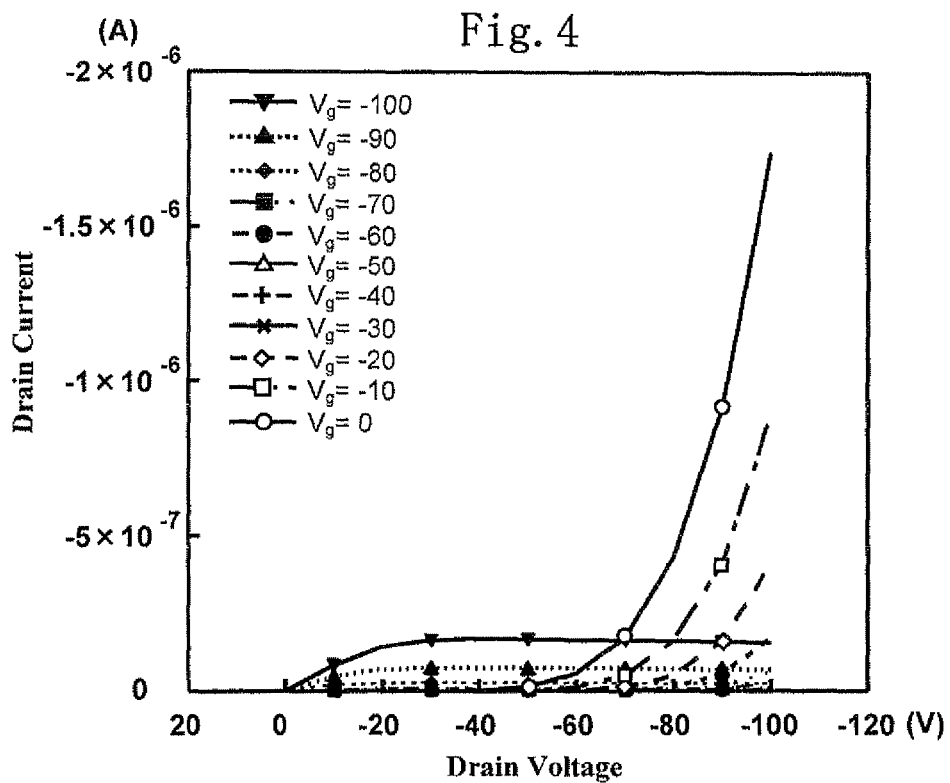
FIG. 4 is a graph showing a relationship between a drain current and a drain voltage of a p-type organic field effect transistor of the present invention.
Figure 5:
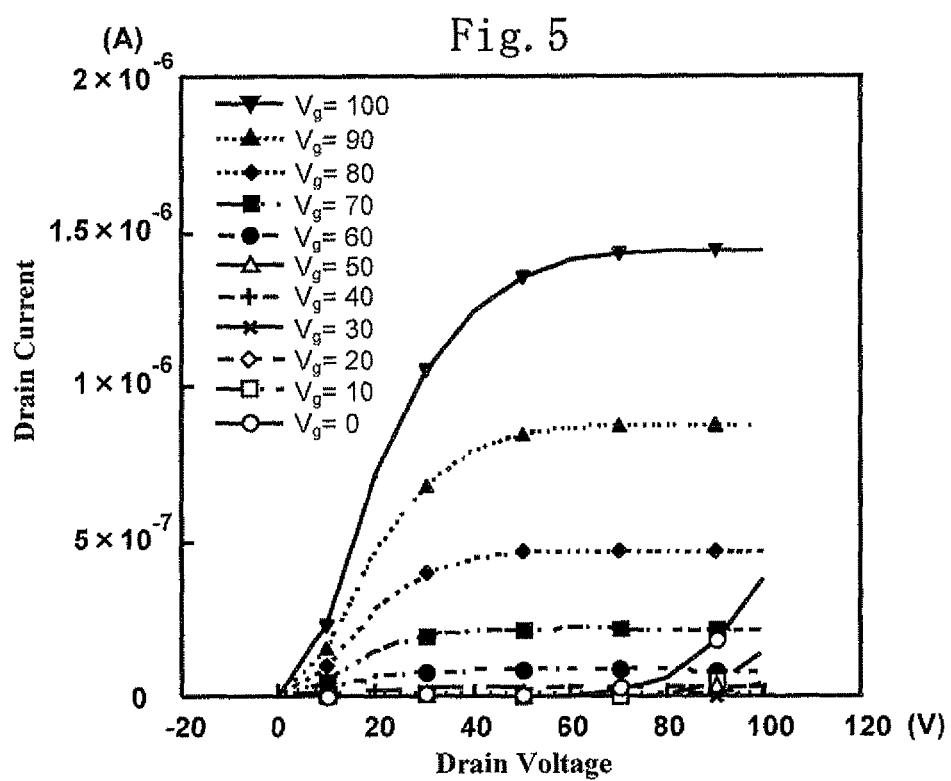
FIG. 5 is a graph showing a relationship between a drain current and a drain voltage of an n-type organic field effect transistor of the present invention.

FIGS. 4 and 5 show relationship between drain current ($I_d$) and drain voltage ($V_d$) at a gate voltage ($V_g$) of −100 to 100V, of organic field effect transistors made of the compound produced in Example 9. It was confirmed that the transistor has characteristics of p-type transistor at $V_g<0$, but n-type characteristics at $V_g>0$. The organic field effect transistor made of the compound produced in Example 9 exhibits ambipolar characteristics.

INDUSTRIAL APPLICABILITY

The thienopyrazine compound of the present invention can be used as organic semiconductor material such as organic field effect transistors, organic light-emitting diodes, photoelectric cells, dye-sensitised solar cells, organic electronic devices, etc. In addition, it can be used as an ambipolar molecule for an inverter circuit and a luminous transistor, which can be utilized for low-power consumption purposes.

What is claimed is:

1. A compound represented by formula (I):

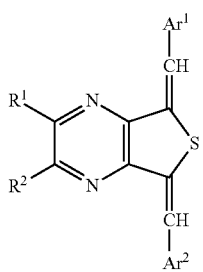

(I)

wherein:
Ar¹ and Ar² each independently represents a functional group selected from the group consisting of a substituted thienyl group, an optionally substituted phenyl group, an optionally substituted naphthyl group, and an optionally substituted dimer made of thienyl, phenyl, or naphthyl groups;
the substituted thienyl group is substituted with, and the optionally substituted phenyl group, the optionally substituted naphthyl group, and the optionally substituted dimer each independently is optionally substituted with one or more substituents selected from the group consisting of a methyl group, ethyl group, n-propyl group, isopropyl group, n-butyl group, isobutyl group, sec-butyl group, tert-butyl group, n-pentyl group, isopentyl group, neopentyl group, tert-pentyl group, n-hexyl group, isohexyl group, 2-ethylhexyl group, n-heptyl group, n-octyl group, n-nonyl group, n-decyl group, cyclopropyl group, cyclopentyl group, cyclohexyl group, cyclooctyl group, trifluoromethyl group, pentafluoroethyl group, a perfluoroalkyl group having 1 to 20 carbons, and 4-trifluoromethylphenyl group; and R¹ and R², together with the carbon atoms to which they are attached, form a ring represented by the following chemical formula:

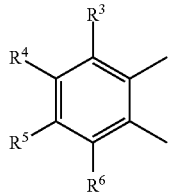

wherein R³, R⁴, R⁵, and R⁶ each independently represents a hydrogen atom, an optionally substituted alkyl group having 1 to 20 carbon atoms, or an optionally substituted aryl group.

2. The compound according to claim 1, represented by formula (II):

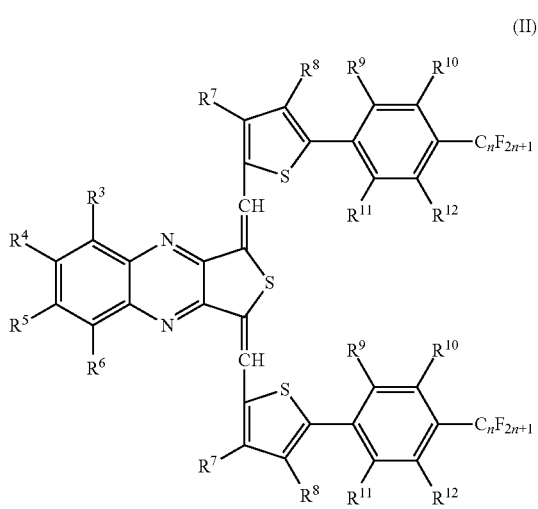

(II)

wherein:
R³, R⁴, R⁵, and R⁶ each independently represents a hydrogen atom, an optionally substituted alkyl group having 1 to 20 carbon atoms, or an optionally substituted aryl group;
R⁷, R⁸, R⁹, R¹⁰, R¹¹, and R¹² each independently represents a hydrogen atom, an optionally substituted hydrocarbon group having 1 to 20 carbon atoms, or an optionally substituted aryl group; and
n is a positive number of 1, 2, 3, 4, 5, 6, 7, 8, 9, 10, 11, 12, 13, 14, 15, 16, 17, 18, 19, or 20.

3. The compound according to claim 1, represented by a formula selected from the group consisting of formula (7), formula (8), formula (9), formula (10), formula (II), formula (12), formula (13), and formula (14):

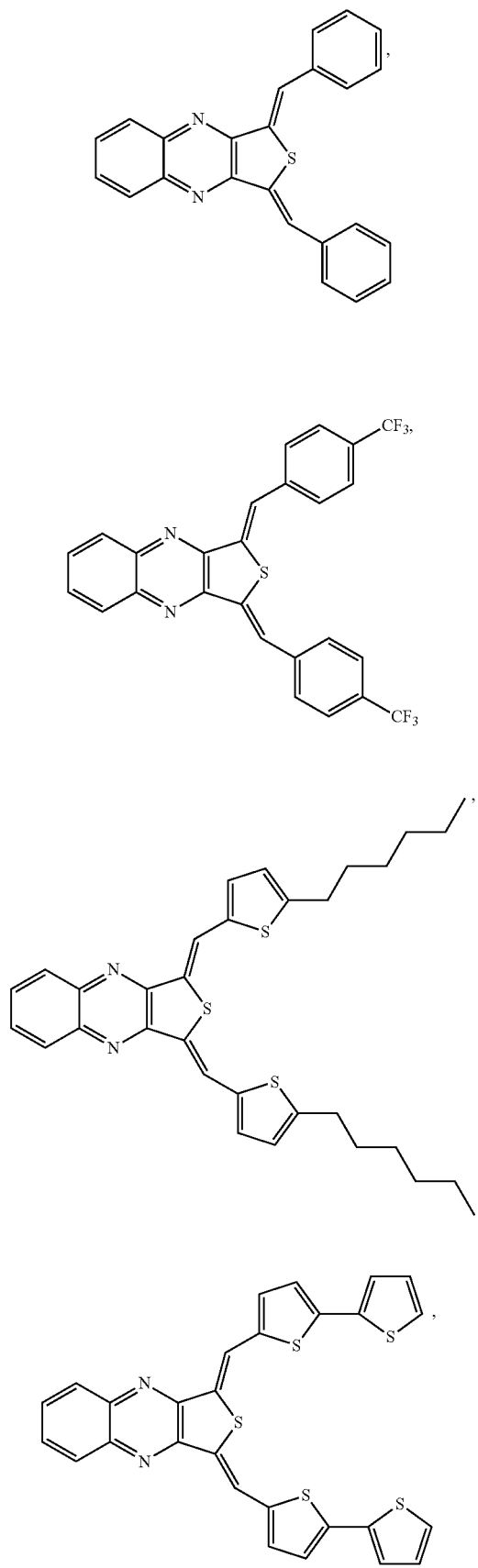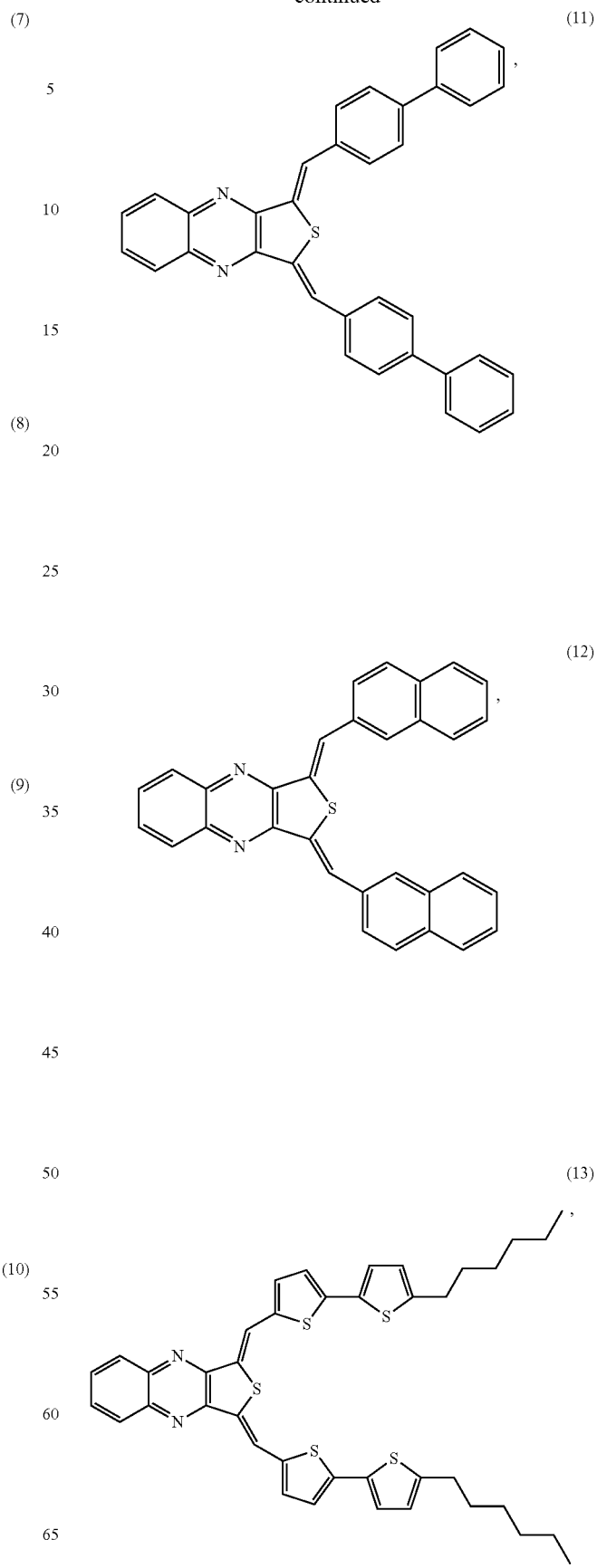

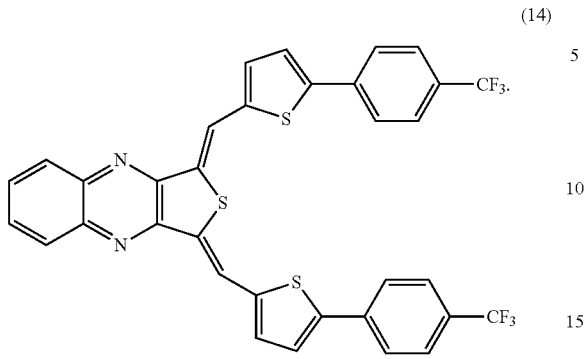

(14)

4. An organic semiconductor material comprising the compound according to claim 1.

5. An organic semiconductor material comprising the compound according to claim 2.

6. An organic semiconductor material containing the compound according to claim 3.

7. An organic field effect transistor comprising an organic semiconductor layer that forms a current path between a source electrode and a drain electrode; the organic semiconductor being separated by an insulator layer from a gate electrode controlling an electric current of the current path on a base plate; and the organic semiconductor layer comprising the compound according to claim 1.

8. The organic field effect transistor according to claim 7, wherein the organic semiconductor layer has an ambipolar characteristic and the compound is represented by chemical formula (II):

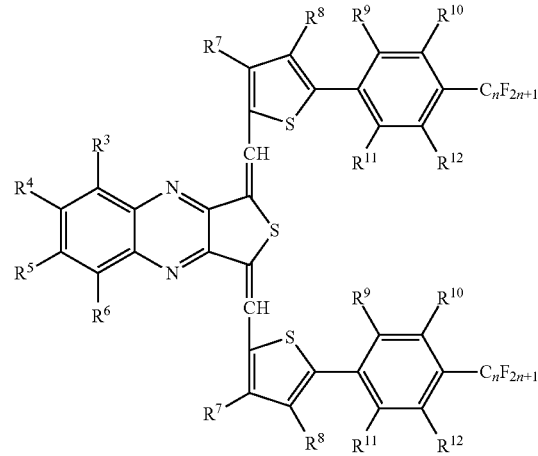

(II)

wherein:

$R^3$, $R^4$, $R^5$, and $R^6$ each independently represents a hydrogen atom, an optionally substituted alkyl group having 1 to 20 carbon atoms, or an optionally substituted aryl group;

$R^7$, $R^8$, $R^9$, $R^{10}$, $R^{11}$, and $R^{12}$ each independently represents a hydrogen atom, an optionally substituted hydrocarbon group having 1 to 20 carbon atoms, or an optionally substituted aryl group;

n is a positive number of 1, 2, 3, 4, 5, 6, 7, 8, 9, 10, 11, 12, 13, 14, 15, 16, 17, 28, 19, or 20.

\* \* \* \* \*